US008937062B2

(12) United States Patent  (10) Patent No.: US 8,937,062 B2
Tyle et al.  (45) Date of Patent: *Jan. 20, 2015

(54) COMPOSITIONS AND METHODS FOR TREATING, REDUCING, AMELIORATING, OR PREVENTING INFECTIONS CAUSED BY ANTIBACTERIAL DRUG-RESISTANT BACTERIA

(75) Inventors: Praveen Tyle, Pittsford, NY (US); Pramod Kumar Gupta, Pittsford, NY (US); Susan E. Norton, Rochester, NY (US); Lynne Brunner, Webster, NY (US); Joseph Blondeau, Saskatoon (CA)

(73) Assignee: Bausch & Lomb Incorporated, Rochester, NY (US)

( * ) Notice: Subject to any disclaimer, the term of this patent is extended or adjusted under 35 U.S.C. 154(b) by 604 days.

This patent is subject to a terminal disclaimer.

(21) Appl. No.: 12/051,289

(22) Filed: Mar. 19, 2008

(65) Prior Publication Data

US 2008/0261900 A1  Oct. 23, 2008

Related U.S. Application Data

(60) Provisional application No. 60/896,082, filed on Mar. 21, 2007.

(51) Int. Cl.
*A01N 43/00* (2006.01)
*A01N 43/46* (2006.01)
*A61K 31/55* (2006.01)

(52) U.S. Cl.
CPC ........................................ *A61K 31/55* (2013.01)
USPC ............. 514/217; 514/31; 514/192; 514/178; 514/217.07; 540/575; 540/597

(58) Field of Classification Search
None
See application file for complete search history.

(56) References Cited

U.S. PATENT DOCUMENTS 5,385,900 A  1/1995 Konno et al.
2002/0187193 A1  12/2002 Roy et al.

OTHER PUBLICATIONS

Lewis, The rise of antibiotic-resistant infection, FDA Consumer magazine , Sep. 1995.*
Basseti et al, Efficacy of the combination of levofloxacin plus ceftazidime in the treatment of hosptital-acquired pneumonia in the Intensive care unit, International journal of antimicrobial agents, vol. 28, 2006, pp. 582-558.*
USA Today "Society for the Advancement of education", Feb. 2001.*
Jensen et al, In vitro Antibiotic susceptibilities of ocular isolates in North and South America, Cornea vol. 17, Issue 1, 1998, pp. 79-87.*
Martin et al, N Engl. J Med. 348:1112-1121.*

Samaha-Khoury et al., "Recent developments in B lactamases and extended spectrum B lactamases," Brit. Med. Journal, (vol. 327), (p. 1209-1213), (Nov. 22, 2003).
Lowy, "Antimicrobial resistance: the example of *Staphylococcus aureus*," Jour. of Clin. Invest., May 2003, (vol. 111), (Issue. 9), (p. 1265-1273).
Jacobs et al., "Prevalence of antimicrobial-resistant pathogens in middle ear fluid: multinational study of 917 children with acute otitis media," Antimic. Agents & Chemo., Mar. 1998, (vol. 42), (Issue. 3), (p. 589-595).
Kaplan et al., "Three-year multicenter surveillance of systemic pneumococcal infections in children," Pediatrics, (vol. 102), (Issue. 3), (p. 538-545), (Sep. 3, 1998).
Martinez et al., "Infectious Diseases InfoAlert—A Desk-Top Reference on Infectious Disease Control," Biomedis International, 2003.
Brunner et al., "In vitro activity of SS734, a novel fluoroquinolone, against pathogens associated with bacterial conjunctivitis," Intl J of Antimicrobial Agents, (vol. 29), (p. S475-S476), (Mar. 1, 2007).
Cambau et al., "Mode of action and resistance of the new fluoroquinolone BOL-303224-A," Intl J of Antimicrobial Agents, (vol. 29), (p. S471), (Mar. 1, 2007).
Brunner et al., "Bactericidal activity of SS734, a novel fluoroquinolone, against pathogens associated with bacterial conjunctivitis," Intl J of Antimicrobial Agents, (vol. 29), (p. S476), (Mar. 1, 2007).
Bratzler et al., "Use of antimicrobial prophylaxis for major surgery," Arch Surg, Feb. 2005, (vol. 140), (p. 174-182).
Modern Cataract Surgery, "Webcache.goggleusercontent.com," (Jul. 20, 2010).
Ho et al., "Increasing resistance of *Streptococcus pneumoniae* to fluoroquinolones: results of a Hong Kong multicentre study in 2000," J of Antimicr Chemo, 2001, (vol. 48), (p. 659-665).
Hoogkamp-Korstanje et al., "Comparative in vitro activity of moxifloxacin against gram-positive clinical isolates," J of Antimicr Chemo, 2000, (vol. 45), (p. 31-39).
Yoshizumi, Satoshi et al. "In Vivo Activity of HSR-903, a New Fluoroquinolone, against Respiratory Pathogens" in AntiMicrob Agents and Chemotherapy, Apr. 1998, pp. 785-788.
Bedos, Jean-Pierre et al. "Efficacy of Trovafloxacin against Penicillin-Susceptible and Multiresistant Strains . . . " in AntiMicrob Agents and Chemotherapy, Apr. 1998, pp. 862-867.
Ho, Pak-Leung et al. "Emergence of Fluoroquinolone Resistance among Multiply Resistant Strains of Streptococcus. . . " in AntiMicrob Agents and Chemother., May 1999, pp. 1310-1313.
Azoulay-Dupuis, E. et al. "Activities of Garenoxacin against Quinolone-Resistant *Streptococcus pneumoniae*. . . " in AntiMicrob Agents and Chemotherapy, Mar. 2004, pp. 765-773.
Hooper, "Mechanisms of fluoroquinolone resistance," Drug Resistance Updates, 1999, (vol. 2). (p. 38-55).
Emmerson et al., "The quinolones: Decades of development and use," J of Antimicrobial Chemotherapy (2003). vol. 51, Suppl. S1, pp. 13-20.
Johnson et al., "Activity of moxifloxacin against clinical isolates of *Streptococcus pneumoniae* from England Wales," J of Antimicrobial Chemotherapy (2001), Vo91. 47, pp. 411-415.

(Continued)

*Primary Examiner* — Wu-Cheng Winston Shen
*Assistant Examiner* — Jean Cornet
(74) *Attorney, Agent, or Firm* — Toan P. Vo

(57) ABSTRACT

Compositions comprise a fluoroquinolone having Formulae I-VIII for treating, reducing, ameliorating, or preventing infections caused by some bacteria that are resistant to an antibacterial drug. Methods for treating, reducing, ameliorating, or preventing such infections use such compositions.

5 Claims, No Drawings

(56) References Cited

OTHER PUBLICATIONS

Miller et al., "In vitro fluoroquinolone resistance in staphylococcal endophthalmitis isolates," Arch Ophthalmolol. (2006), vol. 124, pp. 479-483.

Moniot-Ville et al., "Mechanisms of quinolone resistance in a clinical isolate of *Escherichia coli* highly resistant to fluoroquinolones but susceptible to nalidixic acid," Antimicrobial Agents and Chemotherapy (1991), vol. 35, No. 3, pp. 519-512.

Spigaglia et al., "Molecular analysis of the gyrA and gyrB quinolone resistance—determining regions of fluoroquinolone—resistant *Clostridium difficile* mutants selected in vitro," Antimicrobial Agents and Chemotherapy (2009), vol. 53, No. 6, pp. 2463-2468.

Leeb, M. "A Shot in the Arm" in Nature, vol. 431, Oct. 2004, pp. 892-893.

* cited by examiner

COMPOSITIONS AND METHODS FOR TREATING, REDUCING, AMELIORATING, OR PREVENTING INFECTIONS CAUSED BY ANTIBACTERIAL DRUG-RESISTANT BACTERIA

CROSS REFERENCE

This application claims the benefit of Provisional Patent Application No. 60/896,082 filed Mar. 21, 2007 which is incorporated by reference herein.

BACKGROUND OF THE INVENTION

The present invention relates to compositions and methods for treating, reducing, ameliorating, or preventing infections caused by antibacterial drug-resistant bacteria. In particular, the present invention relates to such compositions comprising quinolone carboxylic acids or derivatives thereof, and methods of using the same. More particularly, the present invention relates to such compositions comprising fluoroquinolone carboxylic acids or derivatives thereof, and methods of using the same.

Bacterial pathogens continue to pose a serious threat to public health as indicated by a worldwide resurgence of bacterial diseases. In some instances, common infections, such as otitis and sinusitis, have become difficult to treat because of increasing bacterial resistance to antibiotics. Such resistance may be attributed to prior widespread, and largely effective, therapeutic and prophylactic use of antibiotics, which, unfortunately, over time has also selected for resistant strains of various bacterial pathogens. Of particular concern to the public health have been the emergence and proliferation of bacterial strains that are resistant to multiple antibiotics in the current arsenal of antimicrobial agents. Such multiantibiotic-resistant ("MAR") bacterial strains include species of Gram-positive bacteria, such as, antibiotic-resistant strains of *Staphylococcus aureus, Enterococcus fecalis,* and *Enterococcus fecium,* which, along with antibiotic-resistant Gram-negative strains of *Escherichia coli,* constitute the most frequent etiological agents of nosocomial (hospital-acquired) diseases, such as septicemia, endocarditis, and infections of wounds and the urinary tract. *S. aureus* is currently the most frequent cause of nosocomial bacteremia and skin or wound infection. *Streptococcus pneumonia,* another Gram-positive bacterium, causes several serious and life-threatening diseases, including a contagious meningitis, bacteremia, and otitis media. Annual mortality from *S. pneumoniae* infection alone is estimated at between 3-5 million persons globally. More recently, clinical accounts of highly aggressive skin and tissue infections by "flesh-eating" strains of Group-A *streptococcus* bacteria, such as *Streptococcus pyogenes,* has heightened the concern and need for new or improved antibacterial agents.

B-lactam antibacterial agents, which comprise four major groups: penicillins, cephalosporins, monobactams, and carbapenems, and work by inhibiting the bacterial cell wall synthesis and thus cell division, are the most common treatment for bacterial infections. However, due to their widespread use, bacterial resistance to these drugs has increased.

As a response to bacterial resistance to β-lactam drugs, other antibacterial agents have been developed that target different components of the bacterial cells. For examples, aminoglycosides, macrolides, tetracyclines, and amphenicols inhibit different aspects of bacterial protein synthesis. Antibacterial glycopeptides (such as vancomycin and cycloserine) inhibit the synthesis of peptidoglycan, a major structural component of Gram-positive bacteria cell walls. Quinolones interfere with cell division by targeting bacterial DNA transcription/replication through inhibition of their DNA gyrase and/or topoisomerase IV. Sulfonamides and diaminopyrimidines interfere with the bacteria's ability to synthesize folic acid, thus inhibiting their ability to synthesize the necessary nucleosides thymine and uridine. J. N. Samaha-Kfoury et al., *Br. Med. J.*, Vol. 327, 1209 (2003).

As new antibacterial drugs are applied, the process of natural selection continues to work in favor of the bacteria strains that have mutated to acquire a tolerance of these new drugs. Nowhere has this issue been of greater concern than with the Gram-positive bacteria pneumococci, enterococci, and staphylococci. *Staphylococcus aureus* is perhaps the pathogen of greatest concern because of its intrinsic virulence, its ability to cause a diverse array of life-threatening infections, and its capacity to adapt to different environmental conditions. The mortality of *S. aureus* bacteremia remains approximately 20-40% despite the availability of effective antimicrobials. *S. aureus* is now the leading overall cause of nosocomial infections and, as more patients are treated outside the hospital setting, is an increasing concern in the community. F. D. Lowy, *J. Clin. Invest.*, Vol. 111, No. 9, 1265 (2003).

Therefore, there is a continued need to develop novel antibacterial agents and improved pharmaceutical compositions that are effective against bacteria that are resistant to some of the common prior-art antibacterial drugs. It is also very desirable to provide novel and more effective compositions and methods for the treatment, reduction, amelioration, or prevention of infections caused by a bacterium that is resistant to at least a prior-art antibacterial drug. In addition, it is also very desirable to provide novel and more effective compositions and methods for the treatment, reduction, amelioration, or prevention of infections caused by some of the Gram-positive bacteria that are resistant to at least an antibacterial drug.

SUMMARY OF THE INVENTION

In general, the present invention provides pharmaceutical compositions and methods of using such compositions for the treatment, reduction, amelioration, or prevention of an infection caused by a bacterium that is resistant to at least a prior-art antibacterial drug.

In one aspect, such compositions comprise at least one member of a family of fluoroquinolones that have Formula I, a salt thereof, or an ester thereof,

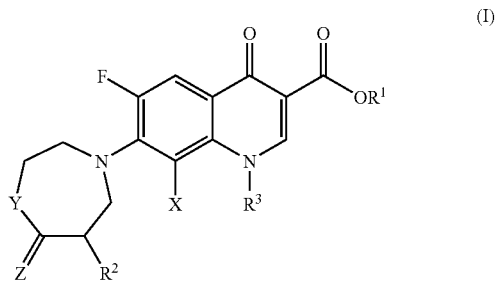

(I)

wherein $R^1$ is selected from the group consisting of hydrogen, unsubstituted lower alkyl groups, substituted lower alkyl groups, cycloalkyl groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; $R^2$ is selected from the group consisting of hydrogen, unsubstituted amino group, and amino groups substituted with one or two lower alkyl groups; $R^3$ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and $NR^4$, wherein $R^4$ is selected from the group consisting of hydrogen, unsubstituted lower alkyl groups, substituted lower alkyl groups, and cycloalkyl groups; and Z is selected from the group consisting of oxygen and two hydrogen atoms.

In still another aspect, a composition of the present invention comprises a single enantiomer of a compound having Formula I.

In still another aspect, a composition of the present invention comprises a member of a family of fluoroquinolones having Formula II, a salt thereof, or an ester thereof,

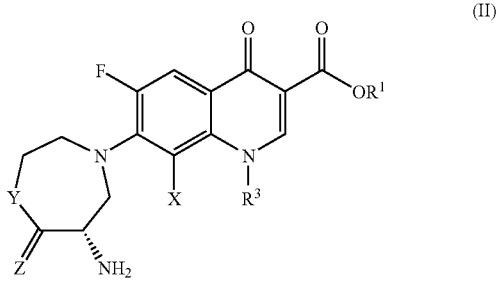

(II)

wherein $R^1$, $R^3$, X, Y, and Z have the meanings as disclosed above.

In still another aspect, the present invention provides a method for treating, reducing, ameliorating, or preventing an infection caused by a bacterium that is resistant to at least a prior-art antibacterial drug. The method comprises administering a composition comprising a fluoroquinolone having Formula I or II to a site of said infection to treat, reduce, ameliorate, or prevent said infection.

In yet another aspect, said at least a prior-art antibacterial drug is a quinolone.

In one embodiment, the method comprises topically administering such a composition. In another embodiment, the method comprises orally administering such a composition.

Other features and advantages of the present invention will become apparent from the following detailed description and claims.

DETAILED DESCRIPTION

As used herein, the term "lower alkyl" or "lower alkyl group" means a $C_1$-$C_{15}$ linear- or branched-chain saturated aliphatic hydrocarbon monovalent group, which may be unsubstituted or substituted. The group may be partially or completely substituted with halogen atoms (F, Cl, Br, or I). Non-limiting examples of lower alkyl groups include methyl, ethyl, n-propyl, 1-methylethyl(isopropyl), n-butyl, n-pentyl, 1,1-dimethylethyl (t-butyl), and the like. It may be abbreviated as "Alk".

As used herein, the term "lower alkoxy" or "lower alkoxy group" means a $C_1$-$C_{15}$ linear- or branched-chain saturated aliphatic alkoxy monovalent group, which may be unsubstituted or substituted. The group may be partially or completely substituted with halogen atoms (F, Cl, Br, or I). Non-limiting examples of lower alkoxy groups include methoxy, ethoxy, n-propoxy, 1-methylethoxy (isopropoxy), n-butoxy, n-pentoxy, t-butoxy, and the like.

The term "cycloalkyl" or "cycloalkyl group" means a stable aliphatic saturated 3- to 15-membered monocyclic or polycyclic monovalent radical consisting solely of carbon and hydrogen atoms which may comprise one or more fused or bridged ring(s), preferably a 3- to 7-membered monocyclic rings. Other exemplary embodiments of cycloalkyl groups include 7- to 10-membered bicyclic rings. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornyl, adamantyl, tetrahydronaphthyl (tetralin), 1-decalinyl, bicyclo[2.2.2]octanyl, 1-methylcyclopropyl, 2-methylcyclopentyl, 2-methylcyclooctyl, and the like.

As used herein, the term "aryl" or "aryl group" means an aromatic carbocyclic monovalent or divalent radical. In some embodiments, the aryl group has a number of carbon atoms from 5 to 24 and has a single ring (e.g., phenyl or phenylene), multiple condensed rings (e.g., naphthyl or anthranyl), or multiple bridged rings (e.g., biphenyl). Unless otherwise specified, the aryl ring may be attached at any suitable carbon atom which results in a stable structure and, if substituted, may be substituted at any suitable carbon atom which results in a stable structure. Non-limiting examples of aryl groups include phenyl, naphthyl, anthryl, phenanthryl, indanyl, indenyl, biphenyl, and the like. It may be abbreviated as "Ar".

The term "heteroaryl" or "heteroaryl group" means a stable aromatic monocyclic or polycyclic monovalent or divalent radical, which may comprise one or more fused or bridged ring(s). In some embodiments, the heteroaryl group has 5-24 members, preferably a 5- to 7-membered monocyclic or 7- to 10-membered bicyclic radical. The heteroaryl group can have from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Non-limiting examples of heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, benzoxazinyl, benzoxazinonyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

In general, the present invention provides a pharmaceutical composition and a method for treating, reducing, ameliorating, or preventing an infection caused by a bacterium that is resistant to at least a prior-art antibacterial agent.

In one embodiment, said bacterium is a Gram-positive bacterium. In another embodiment, said bacterium is a Gram-negative bacterium. In still another embodiment, said bacterium is an anaerobic bacterium.

In one aspect, said prior-art antibacterial agent is selected from the group consisting of drugs of the family of penicillin, drugs of the family of vancomycin, drugs of the family of aminoglycosides, drugs of the family of quinolones, and combinations thereof.

In another aspect, said prior-art antibacterial agent is selected from the group consisting of penicillin, ampicillin, methicillin, vancomycin, gentamicin, ofloxacin, ciprofloxacin, equivalents thereof, and combinations thereof.

In still another aspect, said bacterium that is resistant to a prior-art antibacterial agent is selected from the group consisting of Enterobacteriaceae, *Staphylococcus aureus*, *Streptococcus pneumoniae*, *Haemophilus influenzae*, *Staphylococcus epidermidis*, *Nieisseria gonorrhoea*, and combinations thereof.

In still another aspect, a composition of the present invention comprises at least one member of a family of fluoroquinolones that have Formula I, a salt thereof, or an ester thereof,

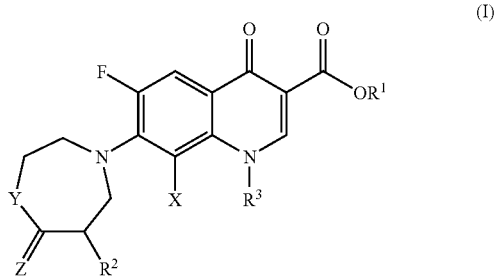

(I)

wherein $R^1$ is selected from the group consisting of hydrogen, unsubstituted lower alkyl groups, substituted lower alkyl groups, cycloalkyl groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; $R^2$ is selected from the group consisting of hydrogen, unsubstituted amino group, and amino groups substituted with one or two lower alkyl groups; $R^3$ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and $NR^4$, wherein $R^4$ is selected from the group consisting of hydrogen, unsubstituted lower alkyl groups, substituted lower alkyl groups, and cycloalkyl groups; and Z is selected from the group consisting of oxygen and two hydrogen atoms.

In one aspect, $R^1$ is selected from the group consisting of hydrogen, $C_1$-$C_5$ (or alternatively, $C_1$-$C_3$) substituted and unsubstituted alkyl groups, $C_3$-$C_{10}$ (or alternatively, $C_3$-$C_5$) cycloalkyl groups, $C_5$-$C_{14}$ (or alternatively, $C_6$-$C_{14}$, or $C_5$-$C_{10}$, or $C_6$-$C_{10}$) substituted and unsubstituted aryl groups, $C_5$-$C_{14}$ (or alternatively, $C_6$-$C_{14}$, or $C_5$-$C_{10}$, or $C_6$-$C_{10}$) substituted and unsubstituted heteroaryl groups, and groups that can be hydrolyzed in living bodies. In one embodiment, $R^1$ is selected from the group consisting of $C_1$-$C_5$ (or alternatively, $C_1$-$C_3$) substituted and unsubstituted alkyl groups.

In another aspect, $R^2$ is selected from the group consisting of unsubstituted amino group and amino groups substituted with one or two $C_1$-$C_5$ (or alternatively, $C_1$-$C_3$) alkyl groups.

In still another aspect, $R^3$ is selected from the group consisting of hydrogen, $C_1$-$C_5$ (or alternatively, $C_1$-$C_3$) substituted and unsubstituted alkyl groups, $C_3$-$C_{10}$ (or alternatively, $C_3$-$C_5$) cycloalkyl groups, $C_1$-$C_5$ (or alternatively, $C_1$-$C_3$) substituted and unsubstituted alkoxy groups, $C_5$-$C_{14}$ (or alternatively, $C_6$-$C_{14}$, or $C_5$-$C_{10}$, or $C_6$-$C_{10}$) substituted and unsubstituted aryl groups, $C_5$-$C_{14}$ (or alternatively, $C_6$-$C_{14}$, or $C_5$-$C_{10}$, or $C_6$-$C_{10}$) substituted and unsubstituted heteroaryl groups, and $C_5$-$C_{14}$ (or alternatively, $C_6$-$C_{14}$, or $C_5$-$C_{10}$, or $C_6$-$C_{10}$) substituted and unsubstituted aryloxy groups. In one embodiment, $R^3$ is selected from the group consisting of $C_3$-$C_{10}$ (or alternatively, $C_3$-$C_5$) cycloalkyl groups.

In yet another aspect, X is selected from the group consisting of Cl, F, and Br. In one embodiment, X is Cl. In another embodiment, X is F.

In a further aspect, Y is $CH_2$. In still another aspect, Z comprises two hydrogen atoms.

In still another aspect, Y is NH, Z is O, and X is Cl.

In another aspect, a composition of the present invention further comprises a pharmaceutically acceptable carrier.

Some non-limiting members of the family of compounds having Formula I are shown in Table 1. Other compounds of the family not listed in Table 1 are also suitable in selected situations.

TABLE 1

Some Selected Fluoroquinolones

| Compound | $R^1$ | $R^2$ | $R^3$ | X | Y | Z |
|---|---|---|---|---|---|---|
| 1 | H | H | $CH_3$ | Cl | $CH_2$ | 2H |
| 2 | H | $NH_2$ | $CH_3$ | Cl | $CH_2$ | 2H |
| 3 | H | $NH_2$ | cyclopropyl | Cl | $CH_2$ | 2H |
| 4 | H | $NH(CH_3)$ | cyclopropyl | Cl | $CH_2$ | 2H |
| 5 | H | $N(CH_3)_2$ | cyclopropyl | Cl | $CH_2$ | 2H |
| 6 | $CH_3$ | $NH_2$ | cyclopropyl | Cl | $CH_2$ | 2H |
| 7 | $C_2H_5$ | $NH_2$ | cyclopropyl | Cl | $CH_2$ | 2H |
| 8 | H | $NH_2$ | cyclopropyl | F | $CH_2$ | 2H |
| 9 | H | $NH_2$ | cyclopropyl | Br | $CH_2$ | 2H |
| 10 | H | $NH(C_3H_5)$ | cyclopropyl | Cl | $CH_2$ | 2H |
| 11 | H | $NH(C_3H_5)$ | cyclopropyl | F | $CH_2$ | 2H |
| 12 | H | $NH_2$ | cyclopentyl | Cl | $CH_2$ | 2H |
| 13 | H | $NH_2$ | cyclopropyl | Cl | $CH_2$ | O |
| 14 | H | $NH_2$ | cyclopropyl | F | $CH_2$ | O |
| 15 | H | $NH_2$ | cyclopropyl | Br | $CH_2$ | O |
| 16 | H | $NH_2$ | cyclopropyl | Cl | $CH(C_3H_5)$ | O |
| 17 | $CH_3$ | $NH_2$ | cyclopropyl | Cl | $CH_2$ | O |
| 18 | $CH_3$ | $NH(CH_3)$ | cyclopropyl | Cl | $CH_2$ | O |
| 19 | $CH_3$ | $N(CH_3)_2$ | cyclopropyl | Cl | $CH_2$ | O |
| 20 | $CH_3$ | $NH(C_3H_5)$ | cyclopropyl | Cl | $CH_2$ | O |
| 21 | $CH_3$ | $NH(C_3H_5)$ | cyclopropyl | Cl | $CH_2$ | O |
| 22 | $CH_3$ | $N(CH_3)(C_2H_5)$ | cyclopropyl | Cl | $CH_2$ | O |

TABLE 1-continued

Some Selected Fluoroquinolones

| Compound | R$^1$ | R$^2$ | R$^3$ | X | Y | Z |
|---|---|---|---|---|---|---|
| 23 | H | NH$_2$ | cyclopropyl | Cl | NH | O |
| 24 | CH$_3$ | NH(CH$_3$) | cyclopropyl | Cl | NH | O |
| 25 | H | 2H | cyclopropyl | Cl | NH | O |

In one embodiment, the fluoroquinolone carboxylic acid included in a composition of the present invention has Formula III.

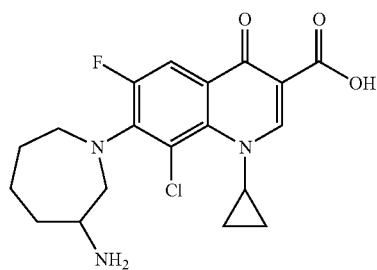

(III)

In another embodiment, the fluoroquinolone carboxylic acid included in a composition of the present invention has Formula IV, V, or VI.

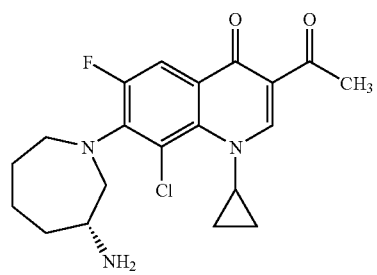

(IV)

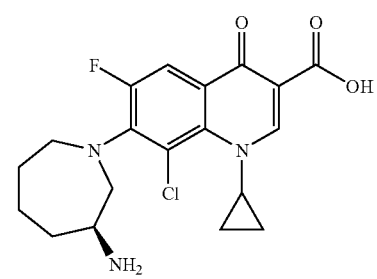

(V)

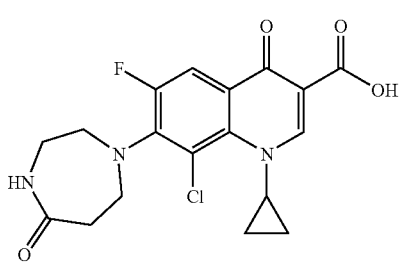

(VI)

In still other embodiments, the fluoroquinolone carboxylic acid included in a composition of the present invention has Formula VII or VIII.

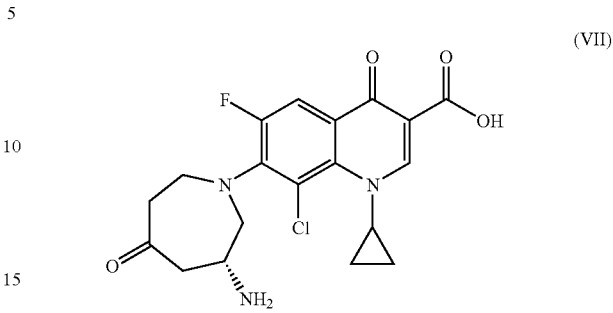

(VII)

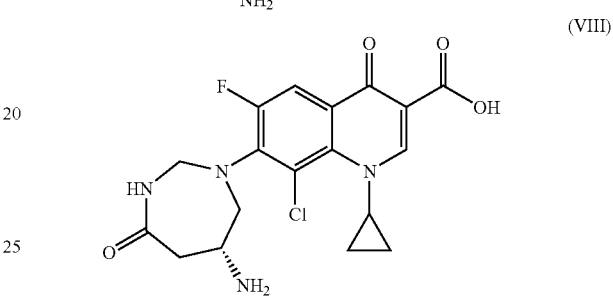

(VIII)

In still another aspect, a composition of the present invention comprises an enantiomer of one of the compounds having Formula I, II, or III.

In still another aspect, a composition of the present invention comprises a mixture of enantiomers of one of the compounds having Formula I, II, or III.

A fluoroquinolone compound disclosed herein can be formulated into a pharmaceutical composition for topical, oral, or systemic administration for the treatment, reduction, amelioration, or prevention of an infection caused by a bacterium that is resistant to at least a prior-art antibacterial drug. Such a composition comprises a fluoroquinolone compound having Formula I, II, II, IV, V, VI, VII, or VIII and a pharmaceutically acceptable carrier for the administration, as can be determined by a person having skill in the art of pharmaceutical formulation. For example, various pharmaceutically acceptable carriers known in the art can be used to formulate a solution, suspension, dispersion, ointment, gel, capsule, or tablet. A fluoroquinolone compound having Formula I, II, II, IV, V, VI, VII, or VIII is particularly suitable for a treatment, reduction, amelioration, or prevention of infections of the ear, eye, or a portion of the upper respiratory tract, caused by bacteria, including, but not being limited to, those bacteria disclosed above. In one embodiment, such a fluoroquinolone is formulated into a solution, ointment, suspension, dispersion, or gel.

In one embodiment, a topical composition of the present invention comprises an aqueous solution or suspension. Typically, purified or deionized water is used. The pH of the composition is adjusted by adding any physiologically acceptable pH adjusting acids, bases, or buffers to within the range of about 3 to about 8.5 (or alternatively, or from about 4 to about 7.5, or from about 4 to about 6.5, or from about 5 to about 6.5). Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers include citrate/dextrose, sodium bicarbonate, ammonium chloride and mixtures of the aforementioned acids and bases. pH buffers are introduced into the composition to maintain a stable pH and to improve product tolerance by the user. In some embodiments, the pH is in the range from about 4 to about 7.5. Biological buffers for various pHs are available, for example, from Sigma-Aldrich. A composition of the present invention can have a viscosity in the range from about 5 to about 100,000 centipoise ("cp") or mPa·s (or alternatively, from about 10 to about 50,000, or from about 10 to about 20,000, or from about 10 to about 10,000, or from about 10 to about 1,000, or from about 100 to about 10,000, or from about 100 to about 20,000, or from about 100 to about 50,000 or from about 500 to about 10,000, or from about 500 to about 20,000 cp).

In another embodiment, a topical composition of the present invention comprises an ointment, emulsion or cream (such as oil-in-water emulsion), or gel.

Ointments generally are prepared using either (1) an oleaginous base; i.e., one consisting of fixed oils or hydrocarbons, such as white petrolatum or mineral oil, or (2) an absorbent base; i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate, hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compound) is added to the formulation at the desired concentration at a point preceding addition of the gelling agent.

The amount of a fluoroquinolone compound, a salt thereof, or an ester thereof, herein disclosed that is incorporated into a formulation of the present invention is not critical; the concentration should be within a range sufficient to permit ready application of the formulation to the affected tissue area in an amount which will deliver the desired amount of compound to the desired treatment site and to provide the desired therapeutic effect. In some embodiments of the present invention, compositions comprise a fluoroquinolone, a salt thereof, or an ester thereof in a concentration in a range from about 0.0001% to 10% by weight (or alternatively, from about 0.001% to about 5%, or from about 0.01% to about 5%, or from about 0.01% to about 2%, or from about 0.01% to about 1%, or from about 0.01% to about 0.7%, or from about 0.01% to about 0.5%, by weight).

Moreover, a topical composition of the present invention can contain one or more of the following: preservatives, surfactants, adjuvants including additional medicaments, antioxidants, tonicity adjusters, viscosity modifiers, and the like.

Preservatives may be used to inhibit microbial contamination of the product when it is dispensed in single or multidose containers, and can include: quaternary ammonium derivatives, (benzalkonium chloride, benzylammonium chloride, cetylmethyl ammonium bromide, cetylpyridinium chloride), benzethonium chloride, organomercury compounds (Thimerosal, phenylmercury acetate, phenylmercury nitrate), methyl and propyl p-hydroxy-benzoates, betaphenylethyl alcohol, benzyl alcohol, phenylethyl alcohol, phenoxyethanol, and mixtures thereof. These compounds are used at effective concentrations, typically from about 0.005% to about 5% (by weight), depending on the preservative or preservatives selected. The amount of the preservative used should be enough so that the solution is physically stable; i.e., a precipitate is not formed, and antibacterially effective.

The solubility of the components, including a fluoroquinolone having Formula I, II, III, IV, V, VI, VII, or VIII, of the present compositions may be enhanced by a surfactant or other appropriate co-solvent in the composition or solubility enhancing agents like cyclodextrins such as hydroxypropyl, hydroxyethyl, glucosyl, maltosyl and maltotriosyl derivatives of α-, β-, and γ-cyclodextrin. In one embodiment, the composition comprises 0.1% to 20% hydroxypropyl-β-cyclodextrin; alternatively, 1% to 15% (or 2% to 10%) hydroxypropyl-β-cyclodextrin. Co-solvents include polysorbates (for example, polysorbate 20, 60, and 80), polyoxyethylene/polyoxypropylene surfactants (e.g., Pluronic® F68, F84, F127, and P103), cyclodextrin, fatty-acid triglycerides, glycerol, polyethylene glycol, other solubility agents such as octoxynol 40 and tyloxapol, or other agents known to those skilled in the art and mixtures thereof. The amount of solubility enhancer used will depend on the amount of fluoroquinolone in the composition, with more solubility enhancer used for greater amounts of fluoroquinolones. Typically, solubility enhancers are employed at a level of from 0.01% to 20% (alternatively, 0.1% to 5%, or 0.1% to 2%) by weight depending on the ingredient.

The use of viscosity enhancing agents to provide the compositions of the invention with viscosities greater than the viscosity of simple aqueous solutions may be desirable to increase absorption of the active compounds by the target tissues or to increase the retention time in the ear. Such viscosity enhancing agents include, for example, polyvinyl alcohol, polyvinyl pyrrolidone, methyl cellulose, hydroxypropylmethyl cellulose, hydroxyethyl cellulose, carboxymethyl cellulose, hydroxypropyl cellulose or other agents know to those skilled in the art. Such agents are typically employed at a level of from 0.01% to 10% (alternatively, 0.1% to 5%, or 0.1% to 2%) by weight.

Suitable surfactants include polyvinyl pyrolidone, polyvinyl alcohol, polyethylene glycol, ethylene glycol, and propylene glycol. Other surfactants are polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). The surfactant helps a topical formulation to spread on the surface of narrow passages.

It is often that an infection is followed by inflammation. Therefore, in another aspect, a composition of the present invention further comprises an anti-inflammatory agent. Anti-inflammatory agents include the well-known glucocorticosteroids and the non-steroidal anti-inflammatory drugs ("NSAIDs").

Non-limiting examples of the glucocorticosteroids are: 21-acetoxypregnenolone, alclometasone, algestone, amcinonide, beclomethasone, betamethasone, budesonide, chloroprednisone, clobetasol, clobetasone, clocortolone, clopredrol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, their physiologically acceptable salts, combinations thereof, and mixtures thereof.

In one embodiment, the preferred glucocorticoids for otic use include dexamethasone, loteprednol, rimexolone, prednisolone, fluorometholone, hydrocortisone, and their derivatives. In another embodiment, the preferred glucocorticoids for nasal use include mometasone, fluticasone, beclomethasone, flunisolide, triamcinolone, budesonide, and their derivatives.

Non-limiting examples of the NSAIDs are: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, S-(5'-adenosyl)-L-methionine, 3-amino-4-hydroxybutyric acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, their physiologically acceptable salts, combinations thereof, and mixtures thereof. In one embodiment, the NSAID is diclofenac, furbiprofen, or ketorolac.

Other non-steroidal anti-inflammatory agents include the cyclooxygenase type II selective inhibitors, such as celecoxib, and etodolac; PAF (platelet activating factor) antagonists, such as apafant, bepafant, minopafant, nupafant, and modipafant; PDE (phosphodiesterase) IV inhibitors, such as ariflo, torbafylline, rolipram, filaminast, piclamilast, cipamfylline, and roflumilast; inhibitors of cytokine production, such as inhibitors of the NF-κB transcription factor; or other anti-inflammatory agents known to those skilled in the art. In one embodiment, the non-steroidal anti-inflammatory agent is celecoxib.

The concentrations of the anti-inflammatory agents contained in the compositions of the present invention will vary based on the agent or agents selected and the type of inflammation being treated. The concentrations will be sufficient to reduce, treat, or prevent inflammation in the targeted tissues following application of a composition of the present invention to those tissues. Such concentrations are typically in the range from about 0.0001 to about 3% by weight (or alternatively, from about 0.01 to about 2%, or from about 0.05% to about 1%, or from about 0.01% to about 0.5%, by weight).

In one aspect, bacterial pathogens that have been isolated from cases of ear infection include *Pseudomonas aeruginosa*, *Staphylococcus aureus*, *Streptococcus pneumoniae*, *Streptococcus pyrogenes*, *Streptococcus faecalis*, *Haemophilus influenzae*, *Moraxella catarahalis*, *Escherichia coli*, *Proteus* species, *Klebsiella* species, and *Enterococcus* species. Several of these species from the isolates have been found to be resistant to a number of antimicrobial drugs. For example, a published study of antimicrobial-resistant pathogens in middle-ear fluid of children with acute otitis media showed that thirty percent of the *S. pneumoniae* isolates were intermediately or fully resistant, and eight percent fully resistant, to penicillin; ten percent of the isolates were resistant to amoxicillin or amoxicillin-clavulanate. M. R. Jacobs et al., *Antimicrobial Agents and Chemotherapy*, Vol. 42, No. 3, 589 (1998). The same study showed that thirty percent of *H. influenzae* isolates produced β-lactamase, and thus, were expected to be resistant to penicillin.

Bacterial pathogens that have been isolated from cases of upper respiratory infections include *Staphylococcus aureus*, *Staphylococcus epidermidis*, *Streptococcus pneumoniae*, *Streptococcus pyrogenes*, *Haemophilus influenzae*, *Peptostreptococcus* species, and *Bacteroides* species.

In a three-year surveillance study (1993-1996) of invasive pneumococcal infections in children, the proportion of *S. pneumoniae* isolates that were nonsusceptible to penicillin or ceftriaxone increased annually, and reached 21% and 9.3%, respectively, for the last year of the study. S. L. Kaplan et al., *Pediatrics*, Vol. 102, No. 3, 538 (1998). A review of community-acquired pneumonia cases in the Asia-Pacific region also revealed increasing resistance of *S. pneumoniae* to penicillin, cephalosporins, and erythromycin. F. J. Martinez, "Infectious Diseases InfoAlert—a Desk-top Reference on Infectious Disease Control," published by Biomedis International, Ltd., 2003.

Compounds having Formulae IV and VI, and prior-art fluoroquinolone antibacterial drugs norfloxacin ("NFLX"), ofloxacin ("OFLX"), and ciprofloxacin ("CPLX") were tested in vitro against some bacteria that are resistant to OFLX, gentamicin ("GM"), penicillin G ("PCG"), or ampicillin ("APC"). A bacterium is said to be resistant to OFLX, GM, PCG, or APC in this testing when the $MIC_{90}$ for the drug is equal to or greater than 8, 16, 2, or 4 μg/ml, respectively. The results are shown in Table 2. Compounds having Formulae IV and VI are generally more effective than NFLX, OFLX, and CPLX, as indicated by the $MIC_{90}$ values; in particular, against OFLX-resistant *S. aureus*. The $MIC_{90}$ values for this test were determined by the agar plate dilution method according to the National Committee for Clinical Laboratory Standards ("NCCLS").

TABLE 2

In vitro Activities of Compounds having Formulae IV and VI, NFLX, OFLX, and CPLX Against Resistant Bacteria

| Organism | Number of Isolates | Drug | MIC₉₀ (μg/ml) Range | Value | Geometric Mean |
|---|---|---|---|---|---|
| OFLX-resistant Enterobacteriaceae | 10 | Compound VI | 16->128 | 32 | 32.0 |
| | | Compound IV | 4-32 | 16 | 11.3 |
| | | NFLX | 16-128 | 128 | 48.5 |
| | | OFLX | 8-64 | 64 | 21.1 |
| | | CPLX | 4-32 | 32 | 10.6 |
| OFLX-resistant S. aureus | 10 | Compound VI | 0.25-8 | 4 | 1.52 |
| | | Compound IV | 0.5-8 | 8 | 2.14 |
| | | NFLX | 64->128 | >128 | 194 |
| | | OFLX | 16->128 | >128 | 104 |
| | | CPLX | 32->128 | >128 | 147 |
| GM-resistant S. aureus | 10 | Compound VI | ≤0.006-4 | 4 | 0.43 |
| | | Compound IV | ≤0.006-8 | 4 | 0.65 |
| | | NFLX | 0.5->128 | >128 | 48.5 |
| | | OFLX | 0.25->128 | >128 | 16.0 |
| | | CPLX | 0.25->128 | >128 | 26.0 |
| GM-resistant P. aeruginosa | 10 | Compound VI | 0.5-64 | 32 | 6.96 |
| | | Compound IV | 0.5-32 | 32 | 5.28 |
| | | NFLX | 0.5-128 | 128 | 5.66 |
| | | OFLX | 0.5-128 | 64 | 6.50 |
| | | CPLX | 0.13-32 | 32 | 1.87 |
| PCG-resistant S. pneumoniae | 10 | Compound VI | 0.13-0.25 | 0.13 | 0.14 |
| | | Compound IV | ≤0.06-0.13 | 0.13 | 0.10 |
| | | NFLX | 2-8 | 8 | 4.29 |
| | | OFLX | 1-2 | 2 | 1.52 |
| | | CPLX | 0.5-2 | 1 | 1.00 |
| APC-resistant Haemophilus influenza. | 10 | Compound VI | ≤0.06 | ≤0.06 | ≤0.06 |
| | | Compound IV | ≤0.06 | ≤0.06 | ≤0.06 |
| | | NFLX | ≤0.06 | ≤0.06 | ≤0.06 |
| | | OFLX | ≤0.06 | ≤0.06 | ≤0.06 |
| | | CPLX | ≤0.06 | ≤0.06 | ≤0.06 |

In a second test, compounds having Formulae IV and V, their racemic mixture, and OFLX were tested in vitro against *S. aureus* strains that are resistant to methicillin or penicillin. The test was conducted according to the guidelines of the Japanese Society of Chemotherapy (1993). The results of this test are shown in Table 3. Compounds having Formula IV or V, and their racemic mixture are more effective against these resistant strains than OFLX, as exhibited by the lower MIC₉₀ values.

TABLE 3

In vitro Activities of Compounds Having Formulae IV, V, Their Racemic Mixture, and OFLX Against Methicillin- or Penicillin-Resistant S. aureus

| Strain | MIC₉₀ (μg/ml) | | | |
|---|---|---|---|---|
| | Racemic Mixture of Compounds IV and V | Compound IV | Compound V | OFLX |
| S. aureus (No. 395)[1] | 0.025 | 0.025 | 0.1 | 0.39 |
| S. aureus (No. 415)[1] | 0.025 | 0.012 | 0.05 | 0.2 |
| S. aureus (No. 419)[1] | 0.05 | 0.025 | 0.1 | 0.39 |
| S. aureus (No. 420)[1] | 0.025 | 0.012 | 0.05 | 0.2 |
| S. aureus (No. 421)[1] | 0.05 | 0.025 | 0.1 | 0.39 |
| S. aureus (ATCC 33591)[1] | 0.05 | 0.025 | 0.1 | 0.39 |
| S. aureus (ATCC 33592)[1] | 0.025 | 0.012 | 0.05 | 0.2 |
| S. aureus (ATCC 33593)[1] | 0.025 | 0.025 | 0.05 | 0.2 |
| S. aureus (ATCC 11632)[2] | 0.025 | 0.025 | 0.05 | 0.2 |
| S. aureus (ATCC 13301)[2] | 0.025 | 0.012 | 0.05 | 0.2 |

Note:
[1] methicillin-resistant;
[2] penicillin-resistant

In a third test, the compound having Formula IV, gatifloxacin ("GTFX"), and moxifloxacin ("MOFX") were tested in vitro against several strains of *H. influenzae, S. aureus, S. epidermidis, S. pneumoniae* strains that are resistant or intermediately resistant to one or more antibacterial drugs ampicillin, methicillin, penicillin, vancomycin, ciprofloxacin, and levofloxacin. The $MIC_{90}$ values were determined according to the broth microdilution method outlined in the Clinical and Laboratory Standards Institute Approved Standard M7-A7 (2006). The results of this test are shown in Table 4. The compound having Formula IV is generally more effective against these resistant strains than GTFX or MOFX, as exhibited by the lower $MIC_{90}$ values.

TABLE 4

In vitro Activities of the Compound Having Formula IV, GTFX, and MOFX Against Certain Resistant Bacteria

| Organism | Number of Isolates | Drug | $MIC_{90}$ (µg/ml) Range | Value | Geometric Mean |
|---|---|---|---|---|---|
| *H. influenzae*, β-lactamase positive | 53 | Compound IV | 0.015-0.06 | 0.03 | 0.027 |
| | | GTFX | 0.08-0.03 | 0.03 | 0.014 |
| | | MOFX | 0.015-0.06 | 0.06 | 0.030 |
| *H. influenzae*, β-lactamase positive, ampicillin-resistant | 25 | Compound IV | 0.015-0.25 | 0.12 | 0.044 |
| | | GTFX | 0.008-0.06 | 0.03 | 0.022 |
| | | MOFX | 0.015-0.12 | 0.12 | 0.047 |
| *S. aureus*, methicillin- and ciprofloxacin-resistant | 24 | Compound IV | 0.5-8 | 8 | 1.542 |
| | | GTFX | 2->8 | >8 | >8 |
| | | MOFX | 1->8 | >8 | 6.924 |
| *S. aureus*, methicillin-resistant and ciprofloxacin-sensitive | 25 | Compound IV | 0.015-1 | 0.06 | 0.033 |
| | | GTFX | 0.03-8 | 0.12 | 0.099 |
| | | MOFX | 0.015-8 | 0.12 | 0.057 |
| *S. aureus*, vancomycin-intermediately resistant | 23 | Compound IV | 0.03-2 | 2 | 0.652 |
| | | GTFX | 0.12->8 | 8 | 3.648 |
| | | MOFX | 0.12->8 | 8 | 2.689 |
| *S. aureus*, vancomycin-resistant | 3 | Compound IV | 1-4 | not applicable | 1.587 |
| | | GTFX | 4->8 | not applicable | 6.350 |
| | | MOFX | 4->8 | not applicable | 6.350 |
| *S. epidermidis*, methicillin-resistant | 64 | Compound IV | 0.015->8 | 8 | 0.397 |
| | | GTFX | 0.06->8 | >8 | 1.428 |
| | | MOFX | 0.06->8 | >8 | 1.125 |
| *S. pneumoniae*, levofloxacin-resistant | 25 | Compound IV | 0.5-8 | 2 | 1.028 |
| | | GTFX | 2->8 | >8 | 5.426 |
| | | MOFX | 2->8 | >8 | 3.681 |
| *S. pneumoniae*, penicillin-intermediately resistant | 26 | Compound IV | 0.06-2 | 0.12 | 0.120 |
| | | GTFX | 0.25->8 | 0.5 | 0.344 |
| | | MOFX | 0.12->8 | 0.25 | 0.209 |
| *S. pneumoniae*, penicillin-resistant | 26 | Compound IV | 0.06-0.12 | 0.12 | 0.108 |
| | | GTFX | 0.12-0.5 | 0.5 | 0.293 |
| | | MOFX | 0.06-0.25 | 0.25 | 0.217 |
| *E. cloacae*, extended-spectrum β-lactamase positive | 15 | Compound IV | 0.25->8 | >8 | 4.595 |
| | | GTFX | 0.03->8 | >8 | 1.579 |
| | | MOFX | 0.06->8 | >8 | 2.749 |

In a fourth test, the anti-bacterial activity of the compound having Formula IV was tested against some methicillin-resistant *S. aureus* bacteria strains and compared to the anti-bacterial activity of three commercially available antibiotics: nadifloxacin ("NDFX"), ofloxacin ("OFLX"), and sparfloxacin ("SPFX"). The results are shown in Table 5 as $MIC_{90}$ values.

TABLE 5

Comparison of In vitro Anti-bacterial Activity of Compound
Having Formula IV, NDFX, OFLX, and SPFX Against
Methicillin-Resistant *S. aureus* Isolates

| | $MIC_{90}$ (μg/ml) | | | |
|---|---|---|---|---|
| Strain | Compound Having Formula IV | NDFX | OFLX | SPFX |
| *Staphylococcus aureus* (ATCC 33591) | 0.012 | 0.006 | 0.05 | 0.024 |
| *Staphylococcus aureus* (ATCC 33592) | 0.05 | 0.05 | 0.39 | 0.1 |
| *Staphylococcus aureus* (ATCC 33593) | 0.012 | 0.024 | 0.2 | 0.024 |
| *Staphylococcus aureus* (No. 395) | 0.006 | 0.024 | 0.2 | 0.05 |
| *Staphylococcus aureus* (No. 415) | 0.05 | 0.1 | 0.78 | 0.2 |
| *Staphylococcus aureus* (No. 419) | 0.1 | 0.39 | 3.13 | 1.56 |
| *Staphylococcus aureus* (No. 420) | 0.1 | 0.78 | 1.56 | 0.78 |
| *Staphylococcus aureus* (No. 421) | 0.2 | 0.78 | 1.56 | 0.39 |

In a fifth test, the anti-bacterial activity of the compound having Formula IV was tested against some opthalmologic antibiotic-resistant clinical bacteria isolates and compared to the anti-bacterial activity of norfloxacin ("NRFX"), OFLX, and CPLX. As disclosed above, most of these bacteria strains are also relevant to infections of the ear and upper respiratory tract. The results are shown in Table 6 as $MIC_{90}$ values.

TABLE 6

Comparison of In vitro Anti-bacterial Activity of Compound
Having Formula IV, Norfloxacin, Ofloxacin, and Ciprofloxacin
Against Some Resistant Clinical Bacteria Isolates

| | $MIC_{90}$ (μg/ml) | | | |
|---|---|---|---|---|
| Antibiotic-resistant Organism Strain | Compound Having Formula IV | NRFX | OFLX | CPLX |
| Ofloxacin-resistant *Enterobacteriaceae* | 16 | 128 | 64 | 32 |
| Ofloxacin-resistant *Staphylococcus aureus* | 8 | >128 | >128 | >128 |
| Gentamicin-resistant *Staphylococcus aureus* | 4 | 128 | 128 | 128 |
| Gentamicin-resistant *Pseudomonas aeruginosa* | 32 | 128 | 64 | 32 |
| Penicillin-resistant *Streptococcus pneumoniae* | 0.13 | 8 | 2 | 1 |

The results show that the compound having Formula IV is more effective than NDFX, OFLX, or CPLX against some antibiotic-resistant bacteria strains that have been found in cases of infection of the ear and upper respiratory tract. Thus, compositions of the present invention can provide novel means to combat antibiotic-resistant bacteria. For example, compositions of the present invention are useful to treat, reduce, ameliorate, or prevent infections of the ear, including otitis externa and otitis media, and infection of the upper respiratory tract, including sinusitis, nasopharyngitis, and oropharyngitis.

In a sixth test, the anti-bacterial activity of the compound having Formula IV was tested against some *S. aureus* and *S. pneumoniae* clinical isolates and compared to the anti-bacterial activity of CPLX, GTFX, levofloxacin ("LVFX"), MOFX, and OFLX. The results are shown in Table 7. The compound having Formula IV is more effective against these bacteria than the tested prior-art fluoroquinolones. Some of these bacteria isolates are resistant to some of the tested prior-art fluoroquinolones as exhibited by the high $MIC_{90}$ values.

TABLE 7

In vitro Activities of Compound Having Formula IV and
Some Commercial Fluoroquinolones Against *S. aureus* and
*S. pneumoniae* Clinical Isolates

| Organism | Number of Isolates | Drug | $MIC_{90}$ (μg/ml) Range | Value |
|---|---|---|---|---|
| *S. aureus* | 49 | Compound IV | 0.015-2 | 0.25 |
| | | CPLX | 0.25->8 | >8 |
| | | GTFX | 0.06->8 | 2 |
| | | LVFX | 0.12->8 | 4 |
| | | MOFX | 0.03->8 | 2 |
| | | OFLX | 0.25->8 | 8 |
| *S. pneumoniae* | 78 | Compound IV | 0.03-0.12 | 0.12 |
| | | CPLX | 0.5-2 | 1 |
| | | GTFX | 0.12-0.5 | 0.25 |
| | | LVFX | 0.5-2 | 1 |
| | | MOFX | 0.06-0.25 | 0.12 |
| | | OFLX | 1-2 | 1 |

The following examples are provided to further illustrate non-limiting compositions of the present invention, and methods of preparing such composition, for the treatment, reduction, amelioration, or prevention of infections.

Example 1

Antibacterial Solution

| Ingredient | Amount (% by weight) |
|---|---|
| Compound having Formula IV | 0.2 |
| Hydroxypropylmethylcellulose ("HPMC") | 0.5 |
| Benzakonium chloride ("BAK") | 0.01 |
| Pluronic ® F127 | 0.1 |
| EDTA | 0.1 |
| NaCl | 0.25 |
| Phosphate buffer (0.05M, pH = 5.0) | q.s. to 100 |

An appropriate proportion (shown in the above table) of Pluronic® F127 is added to phosphate buffer in a sterilized stainless steel jacketed vessel equipped with a stirring mechanism, at a temperature in the range from 50 to 60° C. The resulting buffer solution is heated to 61 to 75° C. At a temperature of about 66° C., an appropriate amount of BAK is added to the buffer solution while mixing three to ten minutes. At a temperature of 75° C., an appropriate amount of the compound having Formula IV is added to the contents of the vessel over a period of three to five minutes while mixing continues. EDTA and NaCl are then added to the mixture while mixing continues for five more minutes at 75° C. The resulting mixture is cooled to 25 to 30° C. The final composition is packaged in appropriate containers.

Example 2

Antibacterial Solution

A procedure similar to that of Example 1 is used to produce this solution.

| Ingredient | Amount (% by weight) |
| --- | --- |
| Compound having Formula IV | 0.35 |
| Mannitol | 4.5 |
| Benzakonium chloride ("BAK") | 0.005 |
| Polysorbate 80 | 0.1 |
| EDTA | 0.05 |
| Sodium acetate | 0.03 |
| Acetic acid | 0.04 |
| Purified water | q.s. to 100 |

Example 3

Antibacterial and Anti-inflammatory Solution

A procedure similar to that of Example 1 is used to produce this solution having the following composition.

| Ingredient | Amount (% by weight) |
| --- | --- |
| Compound having Formula IV | 0.2 |
| Dexamethasone | 0.1 |
| Hydroxypropylmethyl cellulose ("HPMC") | 0.5 |
| Alexidine | 0.01 |
| Brij ® surfactant | 0.1 |
| EDTA | 0.1 |
| Citrate buffer (0.02M sodium citrate, pH = 5.0) | q.s. to 100 |

Example 4

Antibacterial and Anti-inflammatory Solution

A procedure similar to that of Example 1 is used to produce this solution having the following composition.

| Ingredient | Amount (% by weight) |
| --- | --- |
| Compound 8 of Table 1 | 0.3 |
| Colecoxib | 0.15 |
| Propylene glycol | 0.5 |
| Alexidine | 0.01 |
| Tyloxapol | 0.1 |
| EDTA | 0.1 |
| Citrate buffer (0.02M sodium citrate, pH = 5.0) | q.s. to 100 |

Example 5

Antibacterial and Anti-Inflammatory Suspension

A procedure similar to that of Example 1 is used to produce this solution having the following composition.

| Ingredient | Amount (% by weight) |
| --- | --- |
| Compound having Formula IV | 0.3 |
| Triamcinolone, micronized USP | 0.2 |
| Hydroxyethyl cellulose | 0.25 |
| BAK | 0.01 |
| Tyloxapol | 0.05 |
| EDTA | 0.01 |
| NaCl | 0.3 |
| $Na_2SO_4$ | 1.2 |
| Sulfuric acid and/or NaOH | q.s. for pH adjustment to 5.5 |
| Citrate buffer (0.02M sodium citrate, pH = 5.0) | q.s. to 100 |

Example 6

Antibacterial and Anti-Inflammatory Emulsion

A modification of the procedure of Example 1 is used to produce this emulsion having the composition shown in the table below.

Polysorbate 60 (Tween® 60) is added to water in a first sterilized stainless steel jacketed vessel, equipped with a stirring mechanism, at a temperature of 50° C. to 60° C. in amounts corresponding the proportions shown in the table below. The resulting aqueous solution is heated to 61° C. to 75° C. At a temperature of 66° C., benzyl alcohol (a preservative) is added to the aqueous solution while mixing three to ten minutes. At a temperature of 75° C., appropriate amounts of the compound having Formula IV and loteprednole etabonate are added to Mygliol oil in a second sterilized vessel, also equipped with a stirring mechanism, over a period of three to five minutes while stirring continues. Sorbitan monostearate and cetyl stearyl alcohol are added to the oil mixture. The resulting oil mixture is heated to a temperature in the range from 62° C. to 75° C. The oil mixture is then added with vigorous mixing to the aqueous solution in the first vessel at a temperature of 66° C. over a period of three to five minutes. Sodium sulfate and sulfuric acid and/or sodium hydroxide are added to the mixture to adjust pH to 5.5. The resulting composition is cooled to 35° C. to 45° C. and homogenized by mixing with a high shear emulsifier or running through a homogenizer. The composition is further cooled to 25° C. to 30° C. The final composition is packaged in appropriate containers.

| Ingredient | Amount (% by weight) |
| --- | --- |
| Compound having Formula IV | 0.5 |
| Loteprednol etabonate | 0.2 |
| Polysorbate 60 | 1 |
| Sorbitan monostearate (an emulsifier) | 1.5 |
| Cetyl stearyl alcohol (an emulsion stabilizer) | 1.5 |
| Benzyl alcohol | 0.5 |
| Miglyol oil | 14.5 |
| $Na_2SO_4$ | 1.2 |
| Sulfuric acid and/or NaOH | q.s. for pH adjustment to 5.5 |
| Purified water | q.s. to 100 |

Typically, the oil used in an emulsion is a non-irritating emollient oil. Illustrative but non-limiting examples thereof include a mineral oil, vegetable oil, and a reformed vegetable oil of known composition. More specific but non-limiting examples of the oil can be selected from the group consisting of peanut oil, sesame seed oil, cottonseed oil, and a medium chain ($C_6$ to $C_{12}$) triglycerides (e.g., Miglyol Neutral Oils 810, 812, 818, 829, 840, etc., available from Huls America Inc.). Typical emulsifiers employed can be selected from the group consisting of sorbitan monostearate and polysorbate. Preferably, the emulsifiers are nonionic. The emulsifiers can be employed in an amount of 1.5 to 6.5% by weight of the composition, and preferably, 3 to 5% by weight of the composition. The hydrophobic phase of the emulsion can be in an amount of 15 to 25% by weight of the composition, and preferably, 18 to 22% by weight of the composition.

Example 7

Antibacterial Emulsion

A procedure similar to that of Example 6 is used to produce this emulsion having the following composition.

| Ingredient | Amount (% by weight) |
| --- | --- |
| Compound 13 of Table 1 | 0.5 |
| Triamcinolone, micronized USP | 0.2 |
| Polysorbate 60 | 1 |
| Sorbitan monostearate | 1.5 |
| Cetyl stearyl alcohol | 1.5 |
| Benzyl alcohol | 0.5 |
| Miglyol oil | 14.5 |
| $Na_2SO_4$ | 1.2 |
| Sulfuric acid and/or NaOH | q.s. for pH adjustment to 5.5 |
| Purified water | q.s. to 100 |

Example 8

Antibacterial Ointment

A procedure similar to that of Example 1 is used to produce this solution having the following composition.

| Ingredient | Amount (% by weight) |
| --- | --- |
| Compound having Formula IV | 0.3 |
| White petrolatum USP | 50 |
| Propylene glycol | 5 |
| Glycerin | 5 |
| Tween ® 20 | 2 |
| Vitamin E | 1 |
| BAK | 0.1 |
| Mineral oil | q.s. to 100 |

Example 9

Antibacterial Ointment

A procedure similar to that of Example 1 is used to produce this solution having the following composition.

| Ingredient | Amount (% by weight) |
| --- | --- |
| Compound having Formula VI | 0.3 |
| Dexamethasone | 0.15 |
| White petrolatum USP | 50 |
| Propylene glycol | 5 |
| Glycerin | 5 |
| Tween ® 20 | 2 |
| Vitamin E | 1 |
| Vitamin D | 0.5 |
| BAK | 0.1 |
| Mineral oil | q.s. to 100 |

Example 10

Antibacterial Tablet

The ingredients shown in the table below are blended together in a blender, such as a ribbon blender. Other types of blenders that are well known to people skilled in the art of powder mixing also can be used. The mixture is fed through a tableting press at conditions suitable for producing pharmaceutical tablets.

| Ingredient | Amount (% by weight) |
| --- | --- |
| Compound having Formula IV | 0.3 |
| Microcrystalline cellulose | 20 |
| Magnesium stearate | 2 |
| Mannitol | 65 |
| Starch | q.s. to 100 |

The present invention also provides a method for treating, reducing, ameliorating, or preventing an infection caused by a bacterium that is resistant to a prior-art antibacterial drug. The method comprises administering to a subject a composition that comprises a compound selected from the group consisting of fluoroquinolones having Formula I, II, III, IV, V, VI, VII, or VIII, salts thereof, esters thereof, and combinations thereof.

In one aspect, said compound is present in the composition in the range from about 0.0001% to 10% by weight (or alternatively, from about 0.001% to about 5%, or from about 0.01% to about 5%, or from about 0.01% to about 2%, or from about 0.01% to about 1%, or from about 0.01% to about 0.7%, or from about 0.01% to about 0.5%, by weight).

In another aspect, the method further comprises: (a) obtaining from the subject a specimen that includes said bacterium; (b) ascertaining that bacterium is resistant to at least a prior-art antibacterial drug; and (c) administering to said subject a composition that comprises a compound selected from the group consisting of fluoroquinolones having Formula I, II, III, IV, V, VI, VII, or VIII, salts thereof, esters thereof, and combinations thereof.

In another aspect, a composition of the present invention can be used effectively to inhibit the growth or to adversely affect the survival of a bacterium against which a prior-art antibacterial drug has an $MIC_{90}$ value equal to or greater than 1 μg/ml.

In another aspect, a composition of the present invention can be used effectively to inhibit the growth or to adversely affect the survival of a bacterium against which a prior-art antibacterial drug has an $MIC_{90}$ value in the range from about 1 to about 128 μg/ml.

In one embodiment, the present invention provides a method for treating, reducing, ameliorating, or preventing an infection of an eye, ear or respiratory system, wherein such an infection is caused by a bacterium that is resistant to a prior-art antibacterial drug. In one aspect, the method comprises administering one or more drops of a composition of the present invention to the eye, ear canal, nasal cavity, or back of the throat of a subject who has indication of infection or whose risk of infection is indicated. A composition of the present invention can also be formulated into a spray, which can be administered into the otic or nasal cavity of such a subject.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A method for treating, reducing, or ameliorating all infection in a subject, the method comprising administering to said subject in need thereof a composition comprising: (a) a fluoroquinolone having Formula IV or a salt thereof present in an amount effective to treat, reduce, or ameliorate an infection caused by ofloxacin-resistant Enterobacteriaceae with $MIC_{90}$ range of 4-32 μg/ml in vitro, ofloxacin-resistant S. aureus with $MIC_{90}$ range of 0.5-8 μg/ml in vitro, levofloxacin-resistant S. pneumonia with $MIC_{90}$ range of 0.5-8 μg/ml in vitro, gentamicin-resistant *S. aureus* with MIC$_{90}$ range of 0.006-8 µg/ml in vitro, ampicillin-resistant *H. influenza* with MIC$_{90}$ less than or equal to 0.06 µg/ml in vitro, or vancomycin-resistant *S. aureus* with MIC$_{90}$ range of 1-4 µg/ml in vitro; or (b) a fluoroquinolone having Formula VI present in an amount effective to treat, reduce, or ameliorate an infection caused by gentamicin-resistant *S. aureus* with MIC$_{90}$ range of 0.006-4 µg/m in vitro or ampicillin-resistant *H. influenza* with MIC$_{90}$ less than or equal to 0.06 µg/ml in vitro;

the group consisting of gentamycin, vancomycin, ofloxacin, ciprofloxacin, and levofloxacin; and (b) administering to said subject in need thereof a composition comprising (i) a fluoroquinolone having Formula IV or a salt thereof present in an amount effective to treat, reduce, or ameliorate an infection caused by ofloxacin-resistant Enterobacteriaceae with MIC$_{90}$ range of 4-32 µg/ml in vitro, ofloxacin-resistant *S. aureus* with MIC$_{90}$ range of 0.5-8 µg/ml in vitro, levofloxacin-resistant *S. pneumonia* with MIC$_{90}$ range of 0.5-8 µg/ml in vitro, gentamicin-resistant *S. aureus* with MIC$_{90}$ range of 0.006-8 µg/ml in vitro, ampicillin-resistant *H. influenza* with MIC$_{90}$ less than or equal to 0.06 µg/ml in vitro, or vancomycin-resistant *S. aureus* with MIC$_{90}$ range of 1-4 µg/ml in vitro; or (ii) a fluoroquinolone having Formula VI present in an amount effective to treat, reduce, or ameliorate an infection caused by, ofloxacin-resistant *S. aureus* with MIC$_{90}$ range of 0.5-8 µg/ml in vitro or ampicillin-resistant *H. influenza* with MIC$_{90}$ less than or equal to 0.06 µg/ml in vitro;

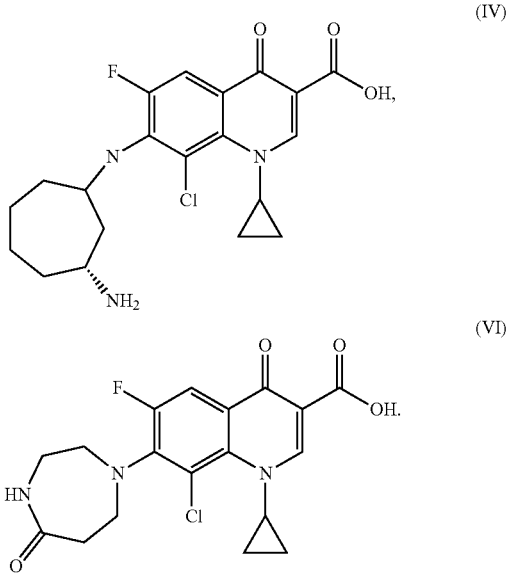

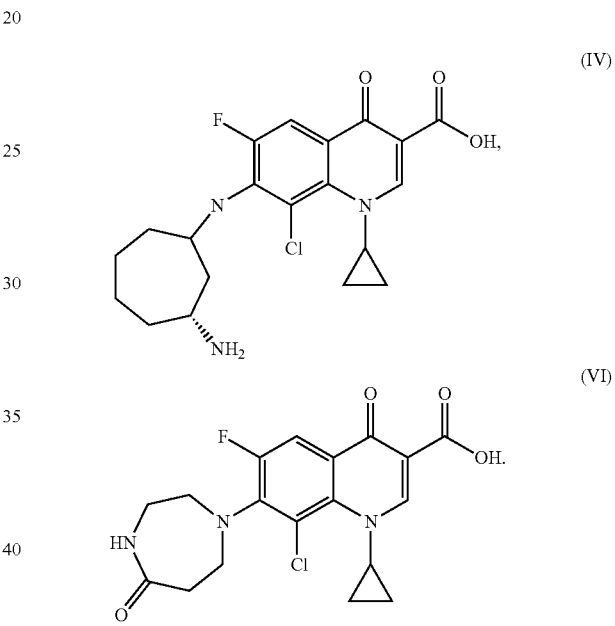

2. The method of claim 1, wherein the composition is administered topically, orally, or systemically.

3. The method of claim 1, where the composition is administered topically.

4. The method of claim 1, wherein the infection is an infection of an eye, ear, respiratory system, or a combination thereof.

5. A method for treating, reducing, or ameliorating an infection in a subject, the method comprising: (a) ascertaining that a specimen from a site of infection contains a bacterium that is resistant to an antibacterial drug that is selected from

* * * * *